US012738033B2

(12) United States Patent
Narasimha Murthy et al.

(10) Patent No.: US 12,738,033 B2
(45) Date of Patent: Sep. 15, 2026

(54) SELF-SUPERVISED TRAINING AT SCALE WITH WEAKLY-SUPERVISED LATENT SPACE STRUCTURE

(71) Applicant: Siemens Healthineers AG, Forchheim (DE)

(72) Inventors: Venkatesh Narasimha Murthy, Hillsborough, NJ (US); Bogdan Georgescu, Princeton, NJ (US); Florin-Cristian Ghesu, Baiersdorf (DE); Mehmet Akif Gulsun, Princeton, NJ (US); Dominik Neumann, Erlangen (DE); Alexandru Constantin Serban, Constanta (RO); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 341 days.

(21) Appl. No.: 18/476,355

(22) Filed: Sep. 28, 2023

(65) Prior Publication Data

US 2025/0111656 A1 Apr. 3, 2025

(51) Int. Cl.
*G06V 10/774* (2022.01)
*G06V 20/50* (2022.01)
(Continued)

(52) U.S. Cl.
CPC .......... *G06V 10/7753* (2022.01); *G06V 20/50* (2022.01); *G06V 20/70* (2022.01); *G16H 50/20* (2018.01); *G06V 2201/03* (2022.01)

(58) Field of Classification Search
CPC .... G06V 10/7753; G06V 20/50; G06V 20/70; G06V 2201/03; G16H 50/20; G16H 30/40
(Continued)

(56) References Cited

U.S. PATENT DOCUMENTS

| | | | | |
|---|---|---|---|---|
| 2022/0208355 A1* | 6/2022 | Li | .......................... | G06N 3/09 |
| 2023/0099938 A1* | 3/2023 | Georgescu | ............... | G06N 7/01 706/12 |
| 2023/0154164 A1 | 5/2023 | Ghesu et al. | | |

(Continued)

OTHER PUBLICATIONS

Self-supervised learning methods and applications in medical imaging analysis: a survey, be Shurrab, Saeed, Duwairi, Rehab, PeerJ Computer Science, 8, e1045, Jul. 19, 2022 (Year: 2022).*

(Continued)

*Primary Examiner* — Jennifer Mehmood
*Assistant Examiner* — Heath E. Wells

(57) ABSTRACT

Systems and methods for performing a medical analysis task using a trained machine learning based task network are provided. Input medical data is received. A medical analysis task is performed using a trained machine learning based task network based on the input medical data. Results of the medical analysis task are output. The trained machine learning based task network is trained by: receiving unannotated training medical data; generating weakly-supervised labels for the unannotated training medical data using one or more trained machine learning based supervised learning networks; training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

20 Claims, 9 Drawing Sheets

(51) Int. Cl.
*G06V 20/70* (2022.01)
*G16H 50/20* (2018.01)

(58) Field of Classification Search
USPC .......................................................... 382/128
See application file for complete search history.

(56) References Cited

U.S. PATENT DOCUMENTS

2023/0281805 A1* 9/2023 Haghighi ............. G06V 10/762 382/128
2024/0402705 A1* 12/2024 Xie ........................ G05D 1/243

OTHER PUBLICATIONS

Litjens et al., "A survey on deep learning in medical image analysis", Medical Image Analysis, 2017, pp. 60-88.
Ericsson et al., "Self-Supervised Representation Learning: Introduction, advances, and challenges", IEEE Signal Processing Magazine, 2022, pp. 42-62.
Ghesu et al., "Self-supervised Learning from 100 Million Medical Images", arXiv:2201.01283v1, 2022, pp. 1-13.
Weng et al., "Self-Supervised Learning", NeurIPS 2021 Tutorial, retrieved online at https://neurips.cc/virtual/2021/tutorial/21895, 2023, 2 pgs.
Chen et al., "A simple framework for contrastive learning of visual representations", arXiv:2002.05709v3, 2020, 20 pgs.
Caron et al., "Unsupervised learning of visual features by contrasting cluster assignments", Advances in Neural Information Processing Systems, 2020, pp. 1-13.
Rudolph et al., "Artificial Intelligence in Chest Radiography Reporting Accuracy: Added Clinical Value in the Emergency Unit Setting Without 24/7 Radiology Coverage", Investigative Radiology, 2022, pp. 1-9.
Soun et al., "Artificial Intelligence and Acute Stroke Imaging", American Society of Neuroradiology, 2020, pp. 1-10.
Gibson et al., "Artificial Intelligence with Statistical Confidence Scores for Detection of Acute or Subacute Hemorrhage on Noncontrast CT Head Scans", Radiology: Artificial Intelligence, 2022, pp. 1-11.
Liu et al., "Simple and principled uncertainty estimation with deterministic deep learning via distance awareness", Advances in Neural Information Processing Systems, 2021, pp. 1-24.
He et al., "Masked autoencoders are scalable vision learners," arXiv:2111.06377v3, 2021, pp. 1-14.

* cited by examiner

Figure 1:
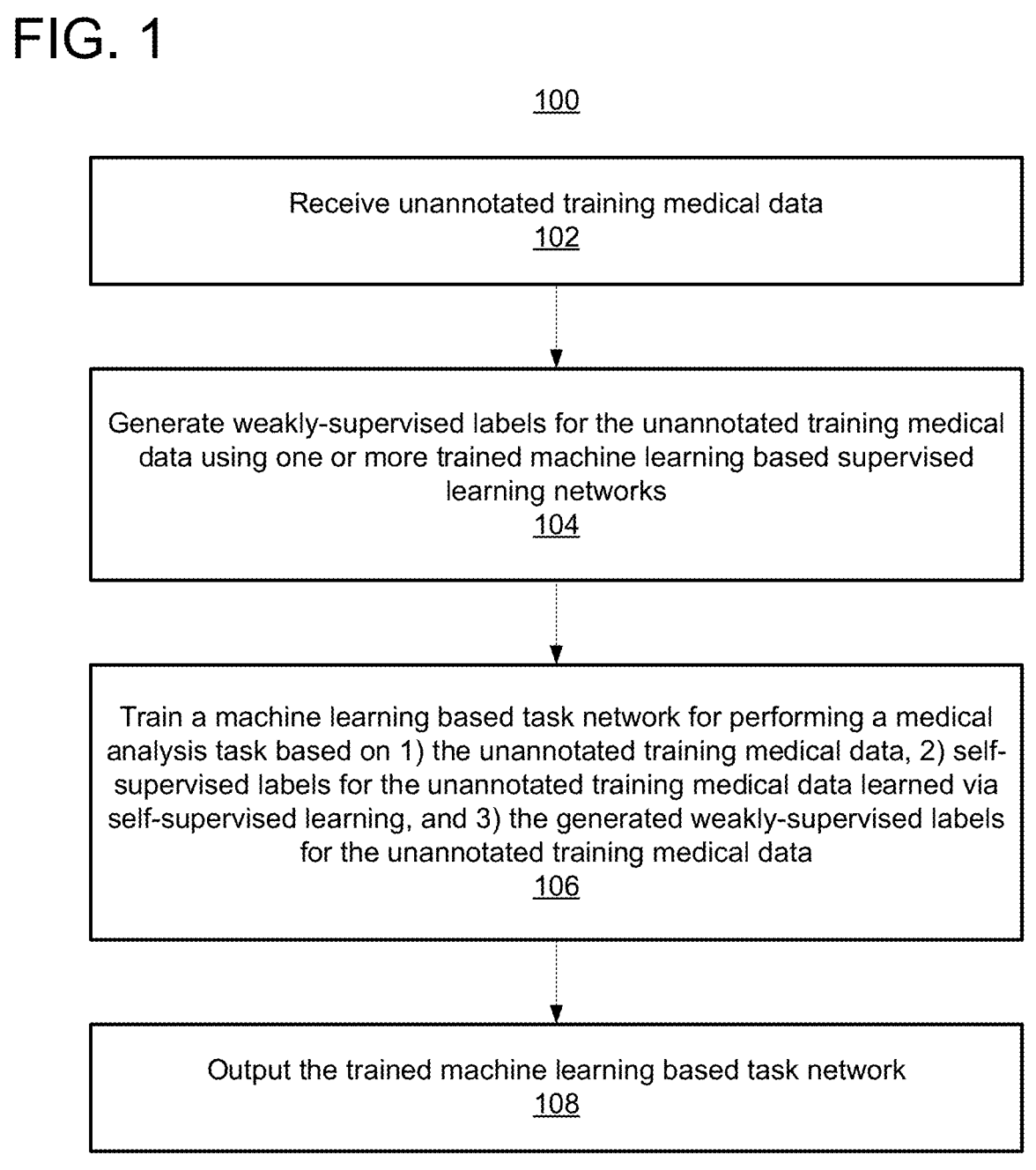

Receive unannotated training medical data
102

Generate weakly-supervised labels for the unannotated training medical data using one or more trained machine learning based supervised learning networks
104

Train a machine learning based task network for performing a medical analysis task based on 1) the unannotated training medical data, 2) self-supervised labels for the unannotated training medical data learned via self-supervised learning, and 3) the generated weakly-supervised labels for the unannotated training medical data
106

Output the trained machine learning based task network
108

Figure 6:
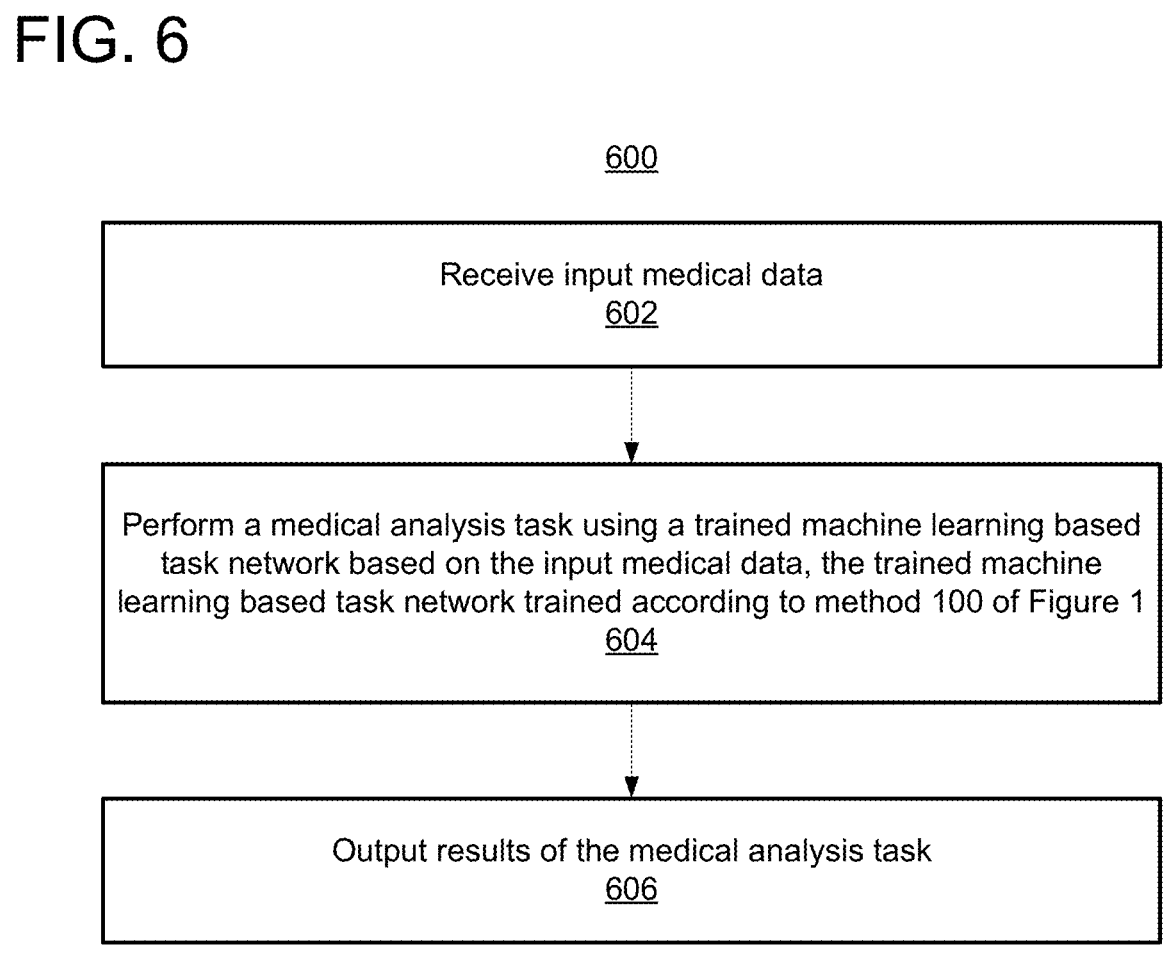

Receive input medical data
602

Perform a medical analysis task using a trained machine learning based task network based on the input medical data, the trained machine learning based task network trained according to method 100 of Figure 1
604

Output results of the medical analysis task
606

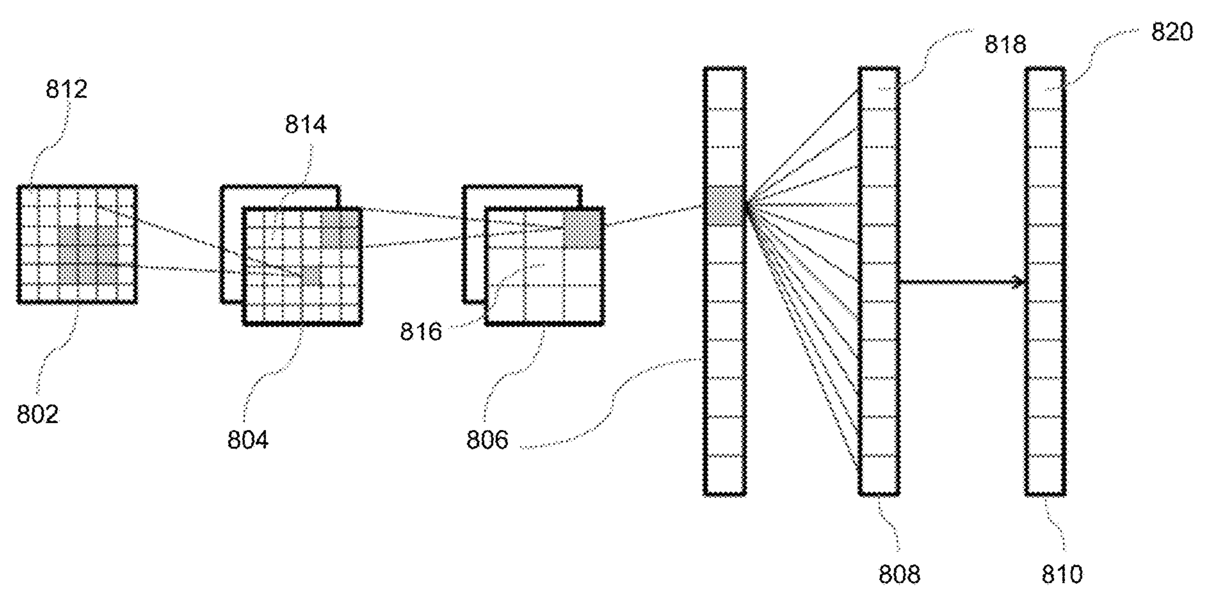
FIG. 8

SELF-SUPERVISED TRAINING AT SCALE WITH WEAKLY-SUPERVISED LATENT SPACE STRUCTURE

TECHNICAL FIELD

The present invention relates generally to training machine learning based networks for performing medical analysis tasks, and in particular to self-supervised training at scale with weakly-supervised latent space structure.

BACKGROUND

Deep learning based networks have been proposed for automatically performing various medical imaging analysis tasks, such as, e.g., classification, segmentation, diagnosis, and treatment support tasks. Conventionally, such deep learning based networks are trained using large amounts of manually annotated training data via supervised learning methods. However, manually annotating such training data is expensive and time-consuming. Recently, self-supervised learning methods have been proposed for training such deep learning based networks using unannotated training data. However, conventional self-supervised learning methods heavily depend on the definition of the pretext tasks and are often missing semantic information in the latent space, limiting the latent space representation power on downstream tasks. Such limitations are particularly apparent in cases involving capture of data abnormalities or labels characterized by subtle data differences, which are not captured in conventional self-supervised learning.

BRIEF SUMMARY OF THE INVENTION

In accordance with one or more embodiments, methods, apparatuses, and computer readable mediums storing computer program instructions for performing a medical analysis task using a trained machine learning based task network are provided. Input medical data is received. A medical analysis task is performed using a trained machine learning based task network based on the input medical data. Results of the medical analysis task are output. The trained machine learning based task network is trained by: receiving unannotated training medical data; generating weakly-supervised labels for the unannotated training medical data using one or more trained machine learning based supervised learning networks; training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

In one embodiment, the machine learning based task network is trained for performing the medical analysis task by assigning the generated weakly-supervised labels to features of a latent space of the machine learning based task network and training the machine learning based task network based on the assigned weakly-supervised labels.

In one embodiment, the machine learning based task network is trained for performing the medical analysis task by training the machine learning based task network using a cost function that incorporates the self-supervised labels and the generated weakly-supervised labels.

In one embodiment, the machine learning based task network is trained for performing the medical analysis task by fitting a probability distribution model to a latent space of the machine learning based task network to capture an uncertainty and training the machine learning based task network based on the uncertainty.

In one embodiment, weakly-supervised labels for the unannotated training medical data are generated by generating initial labels using the one or more trained machine learning based supervised learning networks and filtering the initial labels using one or more out-of-domain probability distribution models to result in labels generated from input data that is in-domain of the one or more trained machine learning based supervised learning networks as generate the weakly-supervised labels.

In one embodiment, the machine learning based task network comprises an encoder and a plurality of decoders. The machine learning based task network is trained for performing the medical analysis task by training the machine learning based task network to perform a plurality of tasks performed respectively using one of the plurality of decoders.

In one embodiment, the machine learning based task network comprises an encoder and a plurality of decoders. The machine learning based task network is trained for performing the medical analysis task by training an initial decoder of the plurality of decoders to generate a reconstructed image based on features generated by the encoder and training one or more additional decoders of the plurality of decoders to respectively perform one or more tasks based on the reconstructed image.

In one embodiment, the machine learning based task network comprises an encoder and a plurality of decoders. The machine learning based task network is trained for performing the medical analysis task by finetuning the machine learning based task network using one or more of the plurality of decoders for domain adaptation.

In accordance with one or more embodiments, methods, apparatuses, and computer readable mediums storing computer program instructions for training a machine learning based task network for performing a medical analysis task are provided. Unannotated training medical data is received. Weakly-supervised labels for the unannotated training medical data are generated using one or more trained machine learning based supervised learning networks. A machine learning based task network is trained for performing a medical analysis task based on 1) the unannotated training medical data, 2) self-supervised labels for the unannotated training medical data learned via self-supervised learning, and 3) the generated weakly-supervised labels for the unannotated training medical data. The trained machine learning based task network is output.

These and other advantages of the invention will be apparent to those of ordinary skill in the art by reference to the following detailed description and the accompanying drawings.

BRIEF DESCRIPTION OF THE DRAWINGS

FIG. 1 shows a method for training a machine learning based task network using self-supervised learning based on weakly-supervised labels for unannotated training medical images, in accordance with one or more embodiments;

FIG. 6 shows a method for performing a medical analysis task using a trained machine learning based task network, in accordance with one or more embodiments;

FIG. 8 shows a convolutional neural network that may be used to implement one or more embodiments.

DETAILED DESCRIPTION

The present invention generally relates to methods and systems for self-supervised training at scale with weakly-supervised latent space structure. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for a self-supervised training workflow for training a machine learning based task network via self-supervised learning and weakly-supervised learning by using weakly-supervised labels generated by machine learning based supervised learning networks. Such weakly-supervised labels are assigned to latent space feature vectors, which are used together with self-supervised labels for training the machine learning based task network. Advantageously, embodiments described herein provide for a trained machine learning based task network with increased accuracy, higher robustness, and accelerated training on any downstream medical imaging analysis task, as compared to conventional machine learning based networks. Such advantages are due to the semantically rich representation that can capture multi-task dependent features provided by the labeled latent space feature vectors.

Figure 2:
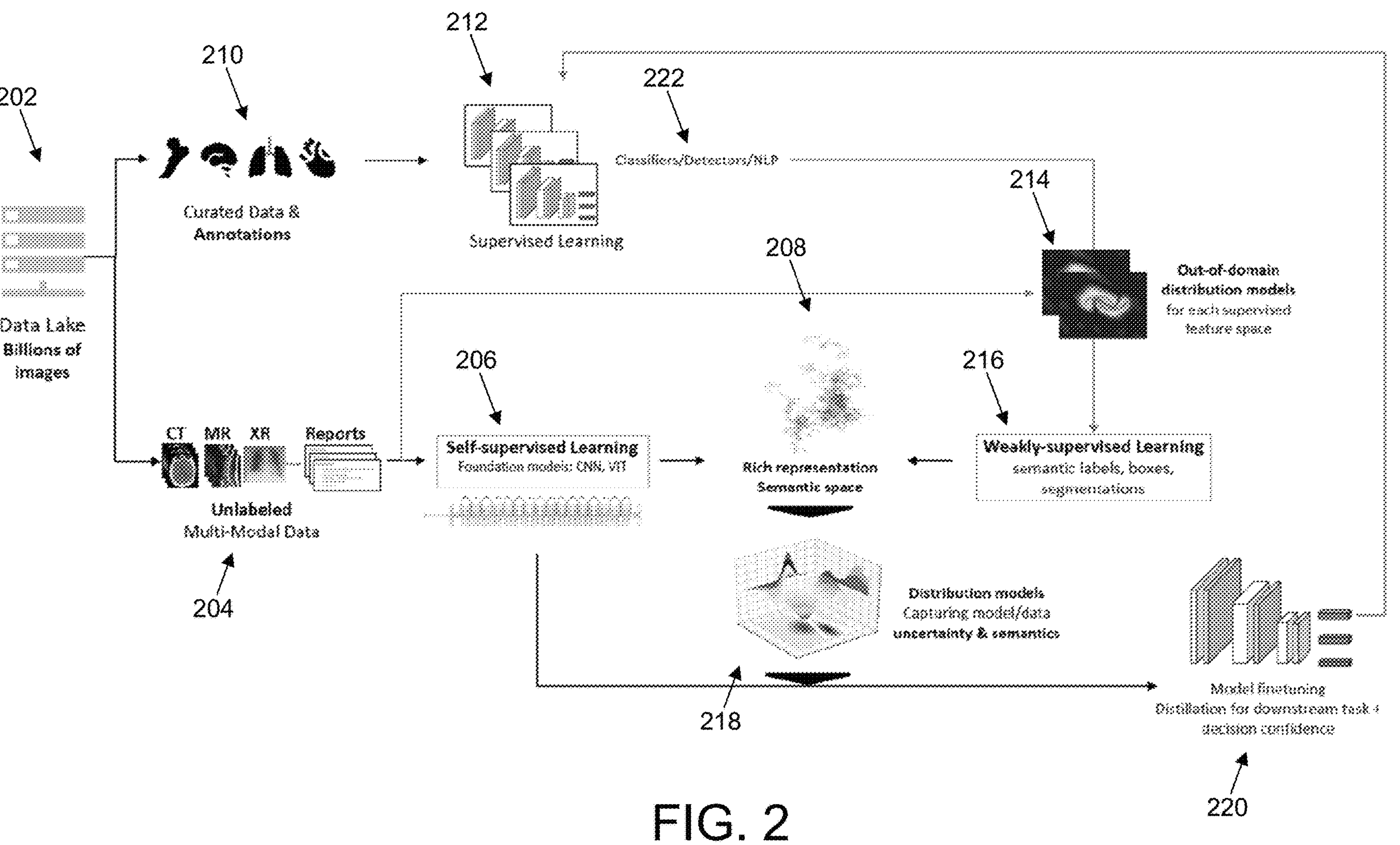
FIG. 2 shows a workflow for training a machine learning based task network using self-supervised learning based on weakly-supervised labels for unannotated training medical data, in accordance with one or more embodiments.

FIG. 1 shows a method 100 for training a machine learning based task network using self-supervised learning based on weakly-supervised labels for unannotated training medical images, in accordance with one or more embodiments. The steps of method 100 may be performed by one or more suitable computing devices, such as, e.g., computer 902 of FIG. 9. FIG. 2 shows a workflow 200 for training a machine learning based task network using self-supervised learning based on weakly-supervised labels for unannotated training medical data, in accordance with one or more embodiments. FIG. 1 and FIG. 2 will be described together. Method 100 of FIG. 1 and workflow 200 of FIG. 2 are performed during a prior offline or training stage to train the machine learning based task network. Once trained, the trained machine learning based task network may be applied to perform a medical analysis task during an online or inference stage, for example, according to method 600 of FIG. 6.

At step 102 of FIG. 1, unannotated training medical data is received. The unannotated training medical data does not include labels for training the machine learning based network. In one example, as shown in workflow 200 of FIG. 2, the unannotated training medical data is unlabeled multi-modal data 204 retrieved from data lake 202. The unannotated training medical data may comprise any suitable medical data for training the machine learning based task network.

In one embodiment, the unannotated training medical data comprises unannotated training medical images. The unannotated training medical images may depict any anatomical object(s) of a patient, such as, e.g., organs, vessels, bones, tumors, or any other suitable anatomical object of interest. The unannotated training medical images may be of any suitable modality or modalities, such as, e.g., CT (computed tomography), MRI (magnetic resonance imaging), US (ultrasound), x-ray, or any other medical imaging modality or combinations of medical imaging modalities. The unannotated training medical images may be 2D (two dimensional) images and/or 3D (three dimensional) volumes.

In one embodiment, the unannotated training medical data comprises unannotated non-imaging medical data. The non-imaging medical data may include, for example, text-based reports associated with the unannotated training medical images.

Figure 9:
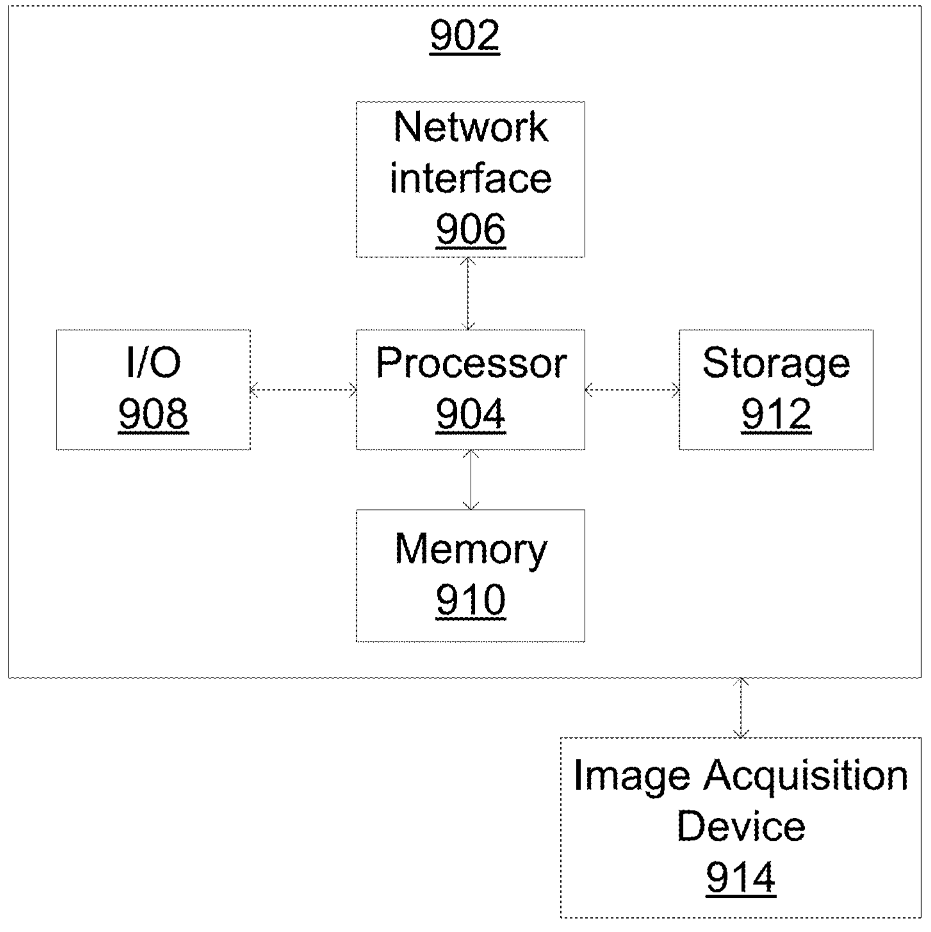
FIG. 9 shows a high-level block diagram of a computer that may be used to implement one or more embodiments.

The unannotated training medical data may be received directly from an image acquisition device, such as, e.g., image acquisition device 914 of FIG. 9 (where the unannotated training medical data comprises unannotated training medical images), may be received by loading previously acquired medical data from a storage or memory of a computer system, or may be received from storage or memory of a remote computer system.

At step 104 of FIG. 1, weakly-supervised labels for the unannotated training medical data are generated using one or more trained machine learning based supervised learning networks. The weakly-supervised labels of the unannotated training medical data are labels generated by the one or more machine learning based supervised learning networks based on the unannotated training medical data. The one or more machine learning based supervised learning networks are machine learning based networks trained via supervised learning using annotated training medical data.

In one example, as shown in workflow 200 of FIG. 2, the one or more trained machine learning based supervised learning networks are classifier/detector/NLP (natural language processing) networks 222. Networks 222 are trained to perform various medical analysis tasks via supervised learning 212 based on annotated training medical data 210 (e.g., images and non-imaging data) of data lake 202. Exemplary medical analysis tasks include pathology and anatomy detection, classification, segmentation, language processing, etc. Once trained, networks 222 are applied to unlabeled multi-modal data 204 to perform the medical analysis tasks. Networks 222 receive as input unlabeled multi-modal data 204 and generate as output results of the medical analysis tasks, which represent the weakly-supervised labels. The results of the medical analysis tasks may include, e.g., overall image labels, segmentation (pixel or voxel) labels, detection boxes for abnormality or regular anatomy, etc. Where the unlabeled multi-modal data 204 comprises non-imaging data (e.g., text reports), the non-imaging data may be parsed using NLP methods.

In one embodiment, to ensure that the one or more trained machine learning based supervised learning networks generate meaningful labels, an out-of-domain probability distribution model is applied for each of the one or more trained machine learning based supervised learning networks to filter initial labels generated by the one or more trained machine learning based supervised learning networks. The out-of-domain probability distribution models determine whether particular input data of the unlabeled multi-modal data 204 is out of distribution of the applied network 222. If the particular input data is out of distribution of the applied network 222, the initial labels generated by the applied network 222 (from the particular input data) are filtered out and removed. If the particular input data is not out of distribution (i.e., in-distribution or in-domain) of the applied network 222, the initial labels generated by the applied network 222 are not filtered out. The remaining unfiltered initial labels represent labels generated from input data that is in-domain of the one or more trained machine learning based supervised learning networks and are output as the weakly-supervised labels utilized at step 104 of FIG. 1. In one example, as shown in workflow 200 of FIG. 2, an out-of-domain distribution model 214 is provided for each of networks 222. In one embodiment, the out-of-domain distribution models 214 is implemented by fitting a Gaussian Process with inducing points in the feature spaces to determine whether the feature space is discriminative to input distances by using network regularization (e.g., spectral regularization). Networks 222 thereby generate results from unlabeled multi-modal data 204 while filtering the results by out-of-domain distribution models 214, resulting in the weakly-supervised labels.

At step 106 of FIG. 1, a machine learning based task network is trained for performing a medical analysis task based on 1) the unannotated training medical data, 2) self-supervised labels for the unannotated training medical data learned via self-supervised learning, and 3) the generated weakly-supervised labels for the unannotated training medical data. The medical analysis task may comprise any suitable medical analysis task. For example, the medical analysis task may comprise medical imaging analysis tasks, such as, e.g., detection, classification, segmentation, etc., or may comprise non-imaging medical analysis tasks, such as, e.g., natural language processing. In one or more embodiments, the machine learning based task network is trained as described with respect to FIGS. 3-4.

In one example, as shown in workflow 200 of FIG. 2, the machine learning based task network is trained (or pretrained) via 1) self-supervised learning 206 to learn self-supervised labels (or pseudo labels) of unlabeled multi-modal data 204 and 2) weakly-supervised learning 216 based on the weakly-supervised labels. Such a trained machine learning based task network provides for rich data representation in a (partially) semantic latent space 208.

Many proposed contrastive self-supervised learning approaches are based on grouping similar samples and distancing dissimilar samples based on self-supervised labels generated from various transformations during the self-supervised learning. In accordance with embodiments described herein, the weakly-supervised labels are assigned to features (i.e., vectors) in the latent space. The weakly-supervised labels are assigned to the features based on the type of the weakly-supervised labels. For example, a classification label may be directly assigned as a label for the corresponding latent features, segmentation labels may be used to generate a label assigned to the latent features based on the percentage of the labeled pixels or voxels present in the input image, detection boxes may be used in addition to generate specific input data crops that are projected into the latent space. The machine learning based task network is trained with any suitable cost function that incorporates both the self-supervised labels and the weakly-supervised labels. An example of such a cost function is normalized cross-entropy loss. To augment the self-supervised cost functions, additional classification heads can be attached to the latent space vector to directly predict the weakly-supervised labels.

In one embodiment, a probability distribution model is fit to the latent space of the machine learning based task network to capture semantic information for specific regions in the latent space and to capture data uncertainty. For example, as shown in workflow 200 of FIG. 2, distribution models 218 are fit to semantic latent space 208 to capture uncertainty and semantics. The uncertainty may be directly incorporated into the cost function for each latent data vector for training the machine learning based task network. For example, cosine similarity may be used in cost functions based on the cross-entropy loss. The cosine similarity may be replaced by directly computing the probability of classification assignment using the fitted distribution models 218. Examples of distribution networks 218 include Gaussian Mixtures, Gaussian Process with inducing points, etc. After pretraining, data clusters in the semantic latent space 208 that do not have a semantic label can be associated with a manually assigned label by examining the data corresponding to representative latent vectors.

In one embodiment, the trained machine learning based task network is finetuned or distilled for a particular downstream medical analysis task(s) and for decision confidence based on the annotated training medical data. For example, the trained machine learning based task network may be finetuned for a particular medical domain or modality, for example, as described with respect to FIG. 5. In one example, as shown in workflow 200 of FIG. 2, the trained machine learning based task network is finetuned at step 220.

At step 108 of FIG. 1, the trained machine learning based task network is output. For example, the trained machine learning based task network can be output by storing the trained machine learning based task network on a memory or storage of a computer system or by transmitting the trained machine learning based task network to a remote computer system. In one example, as shown in workflow 200 of FIG. 2, the trained machine learning based task network may be added to networks 222 for use in a future iteration of workflow 200.

Advantageously, modeling machine learning based task networks through self-supervised and weakly-supervised training at massive scale provides for powerful data representation, discovering underlying multi-modal data structure, and associating latent space structure with semantics, while also provides for modeling operational bounds of the machine learning based task network for increased robustness and confidence of machine learning derived results.

Figure 3:
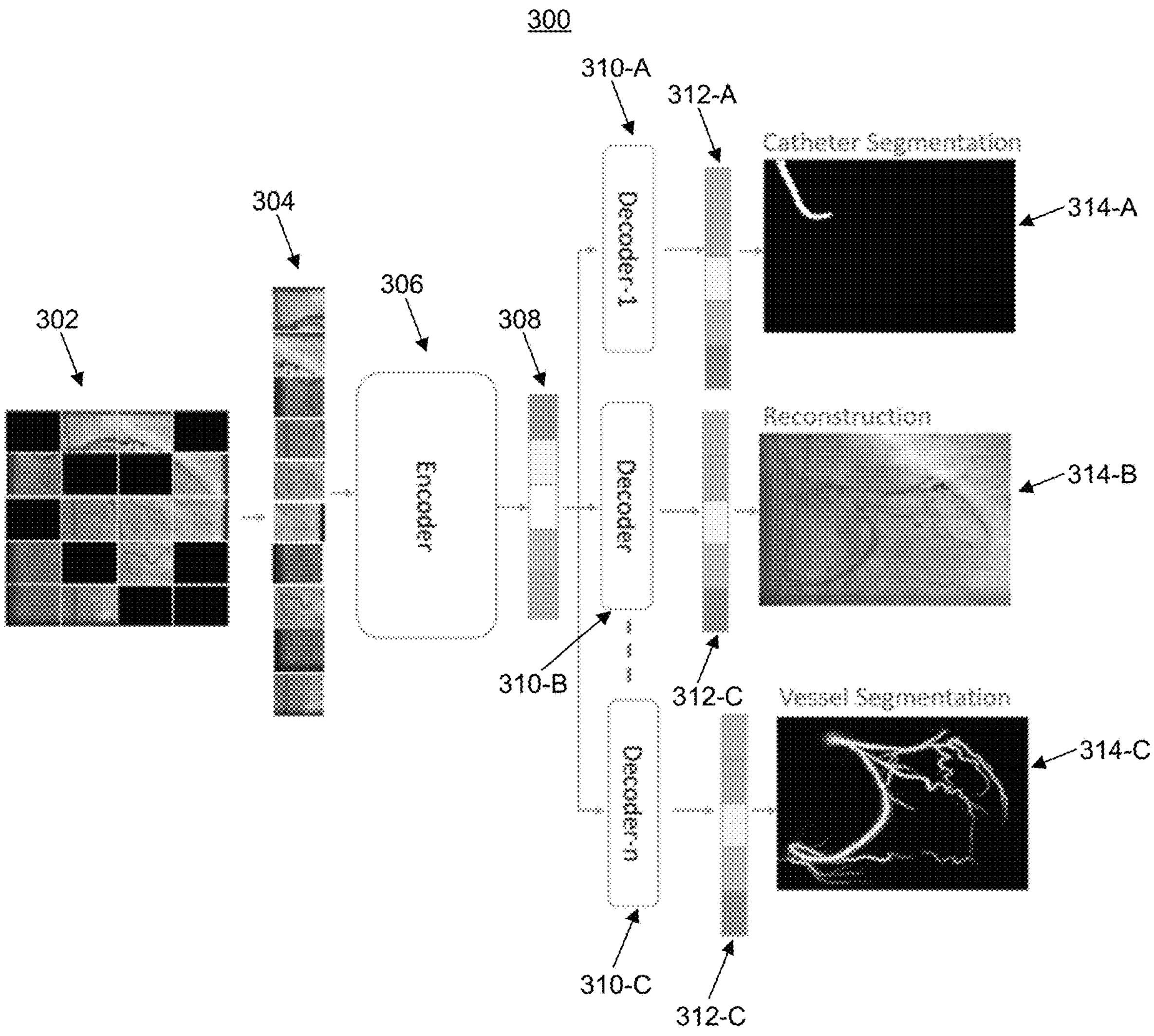
FIG. 3 shows a workflow for multi-task learning using self-supervised and weakly-supervised learning, in accordance with one or more embodiments.

FIG. 3 shows a workflow 300 for multi-task learning using self-supervised and weakly-supervised learning, in accordance with one or more embodiments. In one example, the machine learning based task network trained at step 106 of FIG. 1 comprises encoder 306 and one or more decoders 310-A, 310-B, and 310-C (collectively referred to as decoders 310) of FIG. 3, and workflow 300 of FIG. 3 may be performed at step 106 of FIG. 1.

In workflow 300, encoder 306 is trained on patches 304 extracted from masked training medical image 302. Masked training medical image 302 may be masked according to a masking percentage, which may be user defined or randomly selected to be any value between, e.g., 0% to 90%. In some embodiments, noise may be added to the masked training medical image 302 similar to an autoencoder to train decoder 310-B to reconstruct masked training medical image 302 without the masking and without the noise. In some embodiments, the masked training medical image 302 may instead comprise text-based data with masked tokens. Masked training medical image 302 may be labeled or unlabeled.

Encoder 306 receives as input patches 304 and generates as output latent features 308. Latent features 308 are embeddings representing patches 304. Decoders 310 receive as input latent features 308 and respectively generate as output embedded vectors (or latent space vectors) 312-A, 312-B, and 312-C (collectively referred to as embedded vectors 312). Embedded vectors 312 are features forming a compressed form of images respectively representing results 314-A, 314-B, and 314-C (collectively referred to as results 314) of a medical imaging analysis task. Encoder 306 and decoders 310 may be any suitable encoder/decoder based architecture, such as, e.g., a convolutional network, a transformer network, or any type of neural network.

The medical imaging analysis tasks may be any suitable medical imaging analysis task, such as, e.g., detection, classification, segmentation, etc. In the example shown in workflow 300, the medical imaging analysis tasks comprise catheter segmentation, image reconstruction, and vessel segmentation and results 314-A are catheter segmentation results, results 314-B are a reconstruction of masked training medical image 302 (without the masking), and results 314-C are vessel segmentation results.

In one embodiment, one or more of decoders 310, such as, e.g., decoders 310-A and 310-C, are trained based on weakly-supervised learning by utilizing weakly-supervised labels generated from machine learning based segmentation networks. The weakly-supervised labels are attached to latent features 308 and encoder 306/decoders 310 are trained with a cost function that incorporates the weakly-supervised labels (in addition to self-supervised labels). In one embodiment, one or more of decoders 310, such as, e.g., decoder 310-B, are trained based on unsupervised learning. In one embodiment, one or more of decoders 310 are trained for distillation to match the output of any of the trained machine learning based networks.

In one embodiment, the input masked training medical image 302 may instead comprise video or a sequence of images and the output results 314 may be corresponding output sequences. For example, the input masked training medical image 302 may comprise an angiogram sequence and the output results 314 may comprise catheter/vessel segmentations over time, which takes into account spatial and temporal consistency.

Advantageously, self-supervised multi-task learning utilizes a single encoder 306 with a plurality of decoders 310 to enable encoder 306 to learn meaningful generalized contextual features that are useful for a wide variety of downstream medical imaging analysis tasks.

Figure 4:
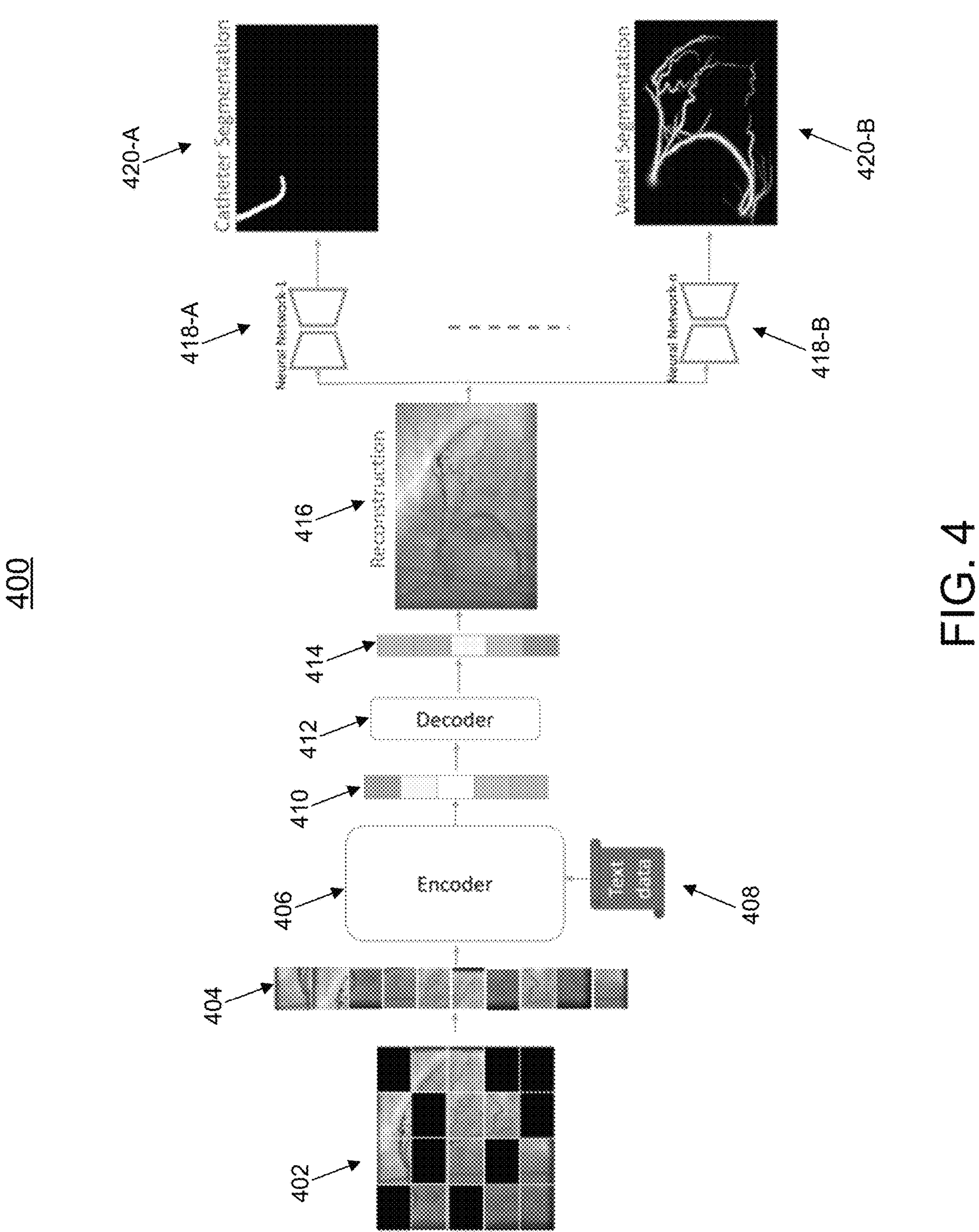
FIG. 4 shows a workflow for multi-task learning with a multi-stage decoder using self-supervised and weakly-supervised learning, in accordance with one or more embodiments.

FIG. 4 shows a workflow 400 for multi-task learning with a multi-stage decoder using self-supervised and weakly-supervised learning, in accordance with one or more embodiments. In one example, the machine learning based task network trained at step 106 of FIG. 1 comprises encoder 406 and one or more decoders 418-A and 418-B (collectively referred to as decoders 418) of FIG. 4, and workflow 400 of FIG. 4 may be performed at step 106 of FIG. 1.

In workflow 400, encoder 406 is trained on patches 404 extracted from masked training medical image 402. Masked training medical image 402 may be masked according to a masking percentage, which may be user defined or randomly selected to be any value between, e.g., 0% to 90%. In some embodiments, noise may be added to the masked training medical image 402 similar to an autoencoder to train decoder 412 to reconstruct masked training medical image 402 without the masking and without the noise. In some embodiments, the masked training medical image 402 may instead comprise text-based data with masked tokens. Masked training medical image 402 may be labeled or unlabeled.

Encoder 406 receives as input patches 404 and optionally text based data 408 and generates as output latent features 410. Latent features 410 are embeddings representing patches 404. Decoder 412 receives latent features 410 and generates as output feature vector 414. A reconstruction image 416 representing an unmasked reconstruction of masked training medical image 402 is generated by, e.g., rearranging feature vector 414. Decoders 418-A and 418-B (collectively referred to as decoders 418) receive as input reconstruction image 416 and respectively generate as output results 420-A and 420-B (collectively referred to as results 420) of a medical imaging analysis task. The medical imaging analysis tasks may be any suitable medical imaging analysis task. In the example shown in workflow 400, the medical imaging analysis tasks comprise catheter segmentation and vessel segmentation and results 420-A are catheter segmentation results and results 420-B are vessel segmentation results.

As shown in FIG. 4, the multi-stage decoder configuration shown in workflow 400 places more emphasis on the image reconstruction task as compared to the single-stage decoder configuration shown in FIG. 3. The first stage decoder 412 will attempt to best generate reconstructed image 416 as a reconstruction of the masked training medical image 402. However, the reconstructed image 416 will likely include some noise or augmentation depending on the input perturbation intensity and type. The second stage decoders 418 should still be able to perform the downstream medical imaging analysis task based on the noisy/augmented reconstruction image 416 while being consistent. The second stage decoders 418 puts emphasis on what matters the most when it comes to image reconstruction and will enforce encoder 406 to focus more on foreground rather than on background or to learn better representation that can generalize well for the downstream medical imaging analysis task.

Figure 5:
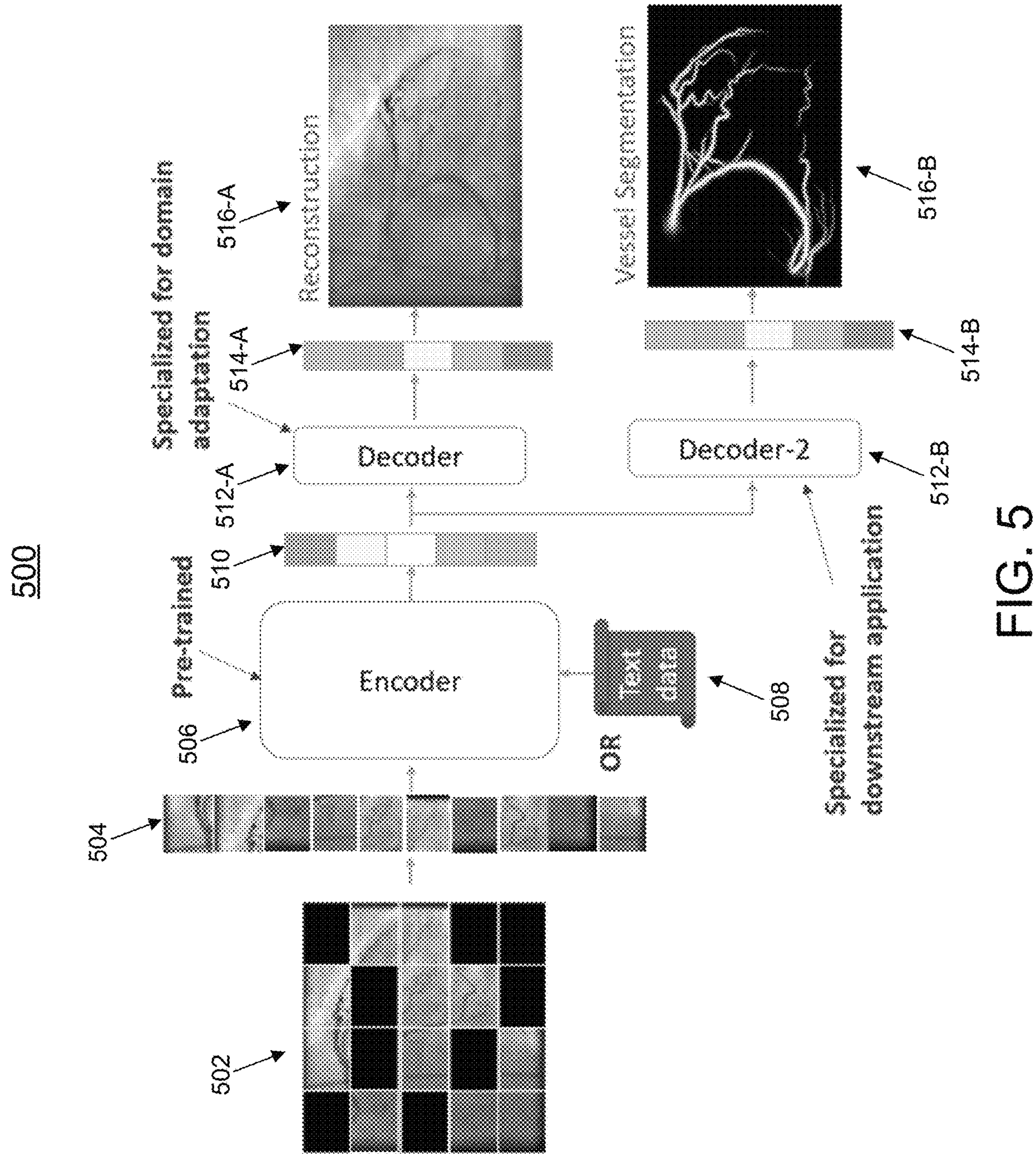
FIG. 5 shows a workflow for finetuning a trained machine learning based task network for domain adaptation, in accordance with one or more embodiments.

FIG. 5 shows a workflow 500 for finetuning a trained machine learning based task network for domain adaptation, in accordance with one or more embodiments. In one example, the machine learning based task network trained at step 106 of FIG. 1 comprises encoder 506 and one or more decoders 512-A and 512-B (collectively referred to as decoders 512) of FIG. 5, and workflow 500 of FIG. 5 may be performed at step 106 of FIG. 1.

Encoder 506 and decoders 512 are pretrained for performing medical imaging analysis tasks for a particular domain or modality. For example, encoder 506 and decoders 512 may be pretrained for image reconstruction and vessel segmentation for MRI and CT. However, performance of encoder 506 and decoders 512 is reduced for out of domain modalities, such as, e.g., x-ray. In accordance with workflow 500, encoder 506 and decoders 512 are finetuned for domain adaptation.

In workflow 500, encoder 506 is finetuned on patches 504 extracted from masked training medical image 502. Masked training medical image 502 may be masked according to a masking percentage, which may be user defined or randomly selected to be any value between, e.g., 0% to 90%. In some embodiments, noise may be added to the masked training medical image 502 similar to an autoencoder to train decoder 512-A to reconstruct masked training medical image 502 without the masking and without the noise. In some embodiments, the masked training medical image 502 may instead comprise text-based data with masked tokens. Masked training medical image 502 may be labeled or unlabeled.

Encoder 506 receives as input patches 504 and/or text-based data 508 and generates as output latent features 510. Latent features 510 are embeddings representing patches 504. Decoders 512 receive as input latent features 510 and respectively generate as output embedded vectors (or latent space vectors) 514-A and 514-B (collectively referred to as embedded vectors 514). Embedded vectors 514 are features forming a compressed form of images respectively representing results 516-A and 516-B (collectively referred to as results 516) of a medical imaging analysis task. Encoder 306 and decoders 310 may be any suitable encoder/decoder based architecture, such as, e.g., a convolutional network, a transformer network, or any type of neural network.

The medical imaging analysis tasks may be any suitable medical imaging analysis task, such as, e.g., detection, classification, segmentation, etc. In the example shown in workflow 5500, the medical imaging analysis tasks comprise image reconstruction and vessel segmentation and results 516-A are a reconstruction of masked training medical image 502 (without the masking) and results 516-B are vessel segmentation results.

In one embodiment, one or more of decoders 516 (e.g., decoder 512-A) are focused of domain adaptation while one or more of decoders 516 (e.g., decoder 5120B) are focused on downstream applications. The domain adaptation may be performed according to the self-supervised/weakly-supervised learning described herein or any other self-supervised learning technique that does not require labels. In another embodiment, a plurality of decoders 516 perform tasks for domain adaptation.

FIG. 6 shows a method 600 for performing a medical analysis task using a trained machine learning based task network, e.g., trained according to method 100 of FIG. 1, in accordance with one or more embodiments. The steps of method 600 may be performed by one or more suitable computing devices, such as, e.g., computer 902 of FIG. 9.

At step 602 of FIG. 6, input medical data is received. The input medical data may comprise one or more medical images and/or non-imaging medical data (e.g., text-based data). The medical images may be of any suitable modality (e.g., CT, MRI, US, x-ray, etc.) and may be 2D and/or 3D medical images. The input medical data may be received directly from an image acquisition device, such as, e.g., image acquisition device 914 of FIG. 9 (where the input medical data comprises medical images), may be received by loading previously acquired medical data from a storage or memory of a computer system, or may be received from storage or memory of a remote computer system.

At step 604 of FIG. 6, a medical analysis task is performed using a trained machine learning based task network based on the input medical data. The trained machine learning based task network is trained according to method 100 of FIG. 1. The medical analysis task may comprise any suitable medical analysis task. For example, the medical analysis task may comprise medical imaging analysis tasks, such as, e.g., detection, classification, segmentation, etc. or a non-imaging medical analysis task, such as, e.g., language processing.

At step 606 of FIG. 6, results of the medical analysis task are output. For example, the results of the medical analysis task can be output by displaying the results of the medical analysis task on a display device of a computer system, storing the results of the medical analysis task on a memory or storage of a computer system, or by transmitting the results of the medical analysis task to a remote computer system.

In one embodiment, embodiments described herein may be applied for chest x-ray classification, abnormality detection, and normal filtering. Machine learning based networks may be applied for abnormality detection and classification in chest radiography, including findings specific to the lung parenchyma (e.g., nodules, consolidation, fibrosis), lung pleura (e.g., pleural effusion, pneumothorax) and bones (e.g., fracture or bone lesions). Such machine learning based networks may also include findings related to anatomical measurements (e.g., cardiomegaly, which leverages the segmentation of the heart). Such machine learning based networks, in addition to anatomy extract networks (e.g., segmentation of the lung parenchyma, ribs, heart, identification of key landmarks such as, e.g., lung apices, spinal processes, etc., identification of the anatomical view-point) can be leveraged to generate weakly-supervised labels for self-supervised learning in accordance with embodiments described herein to train a large scale model with a latent space able to characterize most x-ray abnormalities.

For supervised learning, the data collection does not necessarily need to be limited to radiographs of the chest. Instead, the data collection may be expanded to other body parts of the same modality (e.g., arms, spine, pelvis, legs, etc.). This information is leveraged to learn semantic representations and features that boost the performance of the original models trained with supervised learning.

One exemplary application that may benefit from the embodiments described herein is the filtering of normal or unremarkable exams or exams with no active disease. There is a high variability and degree of subtlety in the appearance of certain findings in chest radiographs, but also the large number of different possible findings. In this context, a purely supervised approach on a dataset of limited size cannot be relied upon.

In one embodiment, embodiments described herein may be applied for NCCT (non-contrast computed tomography) abnormality detection and normal filtering. NCCT of the head is typically used to evaluate the brain structures and determine the presence or absence of pathologies in trauma or stroke evaluations, such as masses, tumors, hemorrhages, or other fluid collections such as abscesses, hydrocephalus, and fractures of the skull. Similar to chest x-ray classification, classifiers trained to detect NCCT abnormalities can be leveraged to generate weakly-supervised labels for self-supervised pretraining with a benefit in filtering out normal NCCT scans automatically. This is an important application in emergency settings for stroke and trauma, where triaging NCCT readings can prioritize potentially abnormal scans.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based model can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
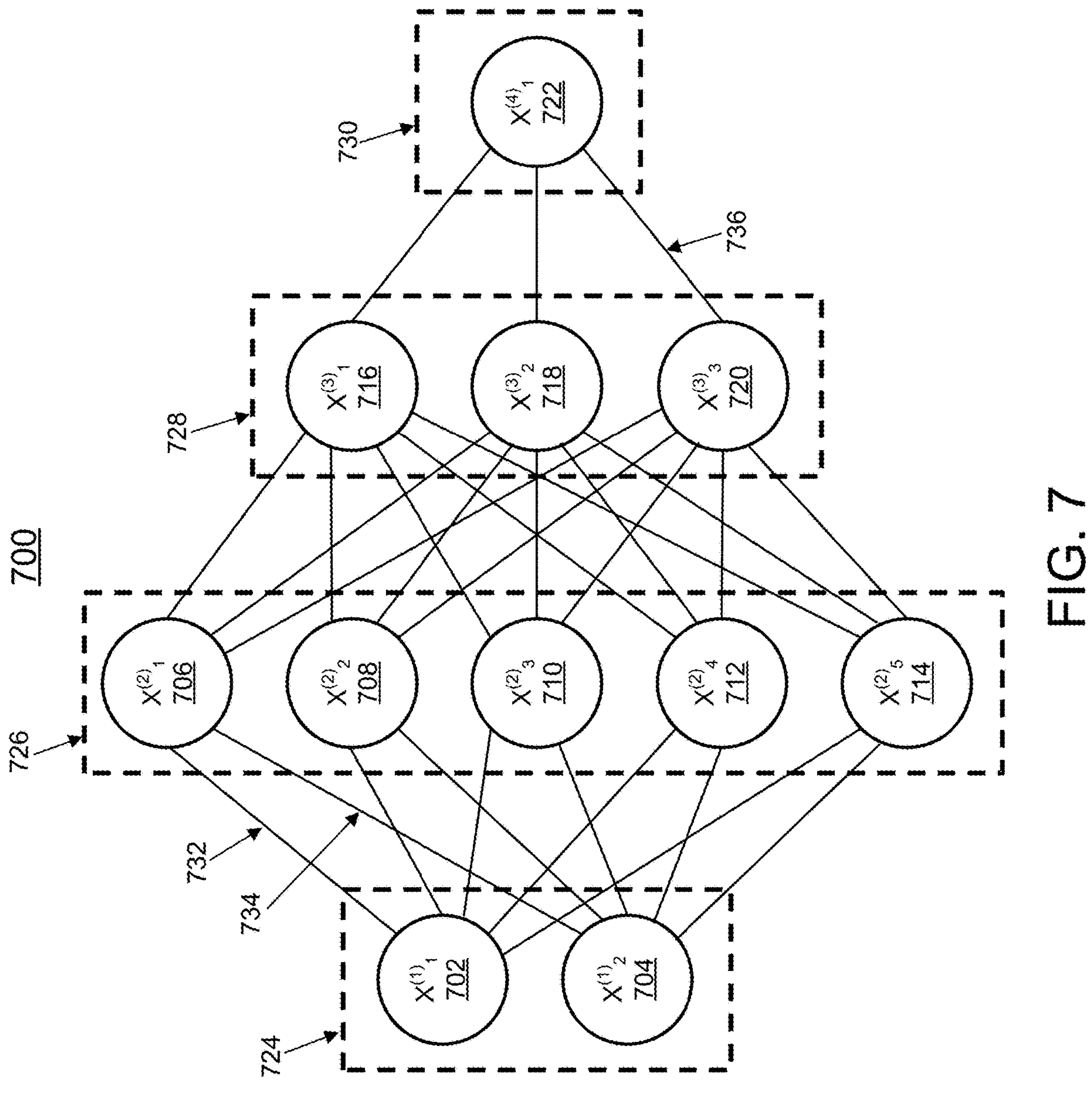
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein, such as, e.g., the one or more trained machine learning based supervised learning networks utilized at step 104 or the machine learning based task network utilized at step 106 of FIG. 1, networks 222 of FIG. 2, encoder 306 and decoders 310 of FIG. 3, encoder 406 and decoders 412 and 418 of FIG. 4, encoder 506 and decoders 512 of FIG. 5, and/or the trained machine learning based task network utilized at step 604 of FIG. 6, may be implemented using artificial neural network 700.

The artificial neural network 700 comprises nodes 702-722 and edges 732, 734, . . . , 736, wherein each edge 732, 734, . . . , 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, . . . , 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, . . . , 736 between the nodes 702-722. In particular, edges 732, 734, . . . , 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}$; denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, . . . , 736 can comprise a weight being a real number, in particular, the weight is a real number within the interval [−1, 1] or within the interval [0, 1]. Here, $w^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n,n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w_{i,j}'^{(n)} = w_{i,j}^{(n)} - \gamma \cdot \delta_j^{(n)} \cdot x_i^{(n)}$$

wherein γ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 730, wherein f' is the first derivative of the activation function, and $y^{(n+1)}_j$ is the comparison training value for the j-th node of the output layer 730.

FIG. 8 shows a convolutional neural network 800, in accordance with one or more embodiments. Machine learning networks described herein, such as, e.g., the one or more trained machine learning based supervised learning networks utilized at step 104 or the machine learning based task network utilized at step 106 of FIG. 1, networks 222 of FIG. 2, encoder 306 and decoders 310 of FIG. 3, encoder 406 and decoders 412 and 418 of FIG. 4, encoder 506 and decoders 512 of FIG. 5, and/or the trained machine learning based task network utilized at step 604 of FIG. 6, may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k = K_k * x^{(n-1)}$ based on the values $x^{(n-1)}$ of the nodes 812 of the preceding layer 802, where the convolution * is defined in the two-dimensional case as $$x_k^{(n)}[i, j] = \left(K_k * x^{(n-1)}\right)[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values $x^{(n)}$ of the nodes 816 of the pooling layer 806 can be calculated based on the values $x^{(n-1)}$ of the nodes 814 of the preceding layer 804 as $$x^{(n)}[i, j] = f\left(x^{(n-1)}[id_1, jd_2], \ldots, x^{(n-1)}[id_1 + d_1 - 1, jd_2 + d_2 - 1]\right)$$

In other words, by using a pooling layer 806, the number of nodes 814, 816 can be reduced, by replacing a number d1-d2 of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g. dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-6. Certain steps or functions of the methods and workflows described herein, including one or more of the steps or functions of FIGS. 1-6, may be performed by a server or by another processor in a network-based cloud-computing system. Certain steps or functions of the methods and workflows described herein, including one or more of the steps of FIGS. 1-6, may be performed by a client computer in a network-based cloud computing system. The steps or functions of the methods and workflows described herein, including one or more of the steps of FIGS. 1-6, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-6, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIGS. 1-6 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 1-6. Accordingly, by executing the computer program instructions, the processor 904 executes the method and workflow steps or functions of FIGS. 1-6. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving input medical data; performing a medical analysis task using a trained machine learning based task network based on the input medical data; and outputting results of the medical analysis task, wherein the trained machine learning based task network is trained by: receiving unannotated training medical data; generating weakly-supervised labels for the unannotated training medical data using one or more trained machine learning based supervised learning networks; training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

Illustrative embodiment 2. The computer-implemented method of illustrative embodiment 1, wherein training the machine learning based task network for performing the medical analysis task comprises: assigning the generated weakly-supervised labels to features of a latent space of the machine learning based task network; and training the machine learning based task network based on the assigned weakly-supervised labels.

Illustrative embodiment 3. The computer-implemented method of any one of the preceding embodiments, wherein training the machine learning based task network for performing the medical analysis task comprises: training the machine learning based task network using a cost function that incorporates the self-supervised labels and the generated weakly-supervised labels.

Illustrative embodiment 4. The computer-implemented method of any one of the preceding embodiments, wherein training the machine learning based task network for performing the medical analysis task comprises: fitting a probability distribution model to a latent space of the machine learning based task network to capture an uncertainty; and training the machine learning based task network based on the uncertainty.

Illustrative embodiment 5. The computer-implemented method of any one of the preceding embodiments, wherein generating weakly-supervised labels for the unannotated training medical data using one or more trained machine learning based supervised learning networks comprises: generating initial labels using the one or more trained machine learning based supervised learning networks; and filtering the initial labels using one or more out-of-domain probability distribution models to result in labels generated from input data that is in-domain of the one or more trained machine learning based supervised learning networks as the weakly-supervised labels.

Illustrative embodiment 6. The computer-implemented method of any one of the preceding embodiments, wherein the machine learning based task network comprises an encoder and a plurality of decoders and training the machine learning based task network for performing the medical analysis task comprises: training the machine learning based task network to perform a plurality of tasks performed respectively using one of the plurality of decoders.

Illustrative embodiment 7. The computer-implemented method of any one of the preceding embodiments, wherein the machine learning based task network comprises an encoder and a plurality of decoders and training the machine learning based task network for performing the medical analysis task comprises: training an initial decoder of the plurality of decoders to generate a reconstructed image based on features generated by the encoder; and training one or more additional decoders of the plurality of decoders to respectively perform one or more tasks based on the reconstructed image.

Illustrative embodiment 8. The computer-implemented method of any one of the preceding embodiments, wherein the machine learning based task network comprises an encoder and a plurality of decoders and training the machine learning based task network for performing the medical analysis task comprises: fine-tuning the machine learning based task network using one or more of the plurality of decoders for domain adaptation.

Illustrative embodiment 9. An apparatus comprising: means for receiving input medical data; means for performing a medical analysis task using a trained machine learning based task network based on the input medical data; and means for outputting results of the medical analysis task, wherein the trained machine learning based task network is trained by: receiving unannotated training medical data; generating weakly-supervised labels for the unannotated training medical data using one or more trained machine learning based supervised learning networks; training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

Illustrative embodiment 10. The apparatus of illustrative embodiment 9, wherein training the machine learning based task network for performing the medical analysis task comprises: assigning the generated weakly-supervised labels to features of a latent space of the machine learning based task network; and training the machine learning based task network based on the assigned weakly-supervised labels.

Illustrative embodiment 11. The apparatus of any one of illustrative embodiments 9-10, wherein training the machine learning based task network for performing the medical analysis task comprises: training the machine learning based task network using a cost function that incorporates the self-supervised labels and the generated weakly-supervised labels.

Illustrative embodiment 12. The apparatus of any one of illustrative embodiments 9-11, wherein training the machine learning based task network for performing the medical analysis task comprises: fitting a probability distribution model to a latent space of the machine learning based task network to capture an uncertainty; and training the machine learning based task network based on the uncertainty.

Illustrative embodiment 13. The apparatus of any one of illustrative embodiments 9-12, wherein generating weakly-supervised labels for the unannotated training medical data using one or more trained machine learning based supervised learning networks comprises: generating initial labels using the one or more trained machine learning based supervised learning networks; and filtering the initial labels using one or more out-of-domain probability distribution models to result in labels generated from input data that is in-domain of the one or more trained machine learning based supervised learning networks as the weakly-supervised labels.

Illustrative embodiment 14. A non-transitory computer readable medium storing computer program instructions, the computer program instructions when executed by a processor cause the processor to perform operations comprising: receiving input medical data; performing a medical analysis task using a trained machine learning based task network based on the input medical data; and outputting results of the medical analysis task, wherein the trained machine learning based task network is trained by: receiving unannotated training medical data; generating weakly-supervised labels for the unannotated training medical data using one or more trained machine learning based supervised learning networks; training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

Illustrative embodiment 15. The non-transitory computer readable medium of illustrative embodiment 14, wherein training the machine learning based task network for performing the medical analysis task comprises: assigning the generated weakly-supervised labels to features of a latent space of the machine learning based task network; and training the machine learning based task network based on the assigned weakly-supervised labels.

Illustrative embodiment 16. The non-transitory computer readable medium of any one of illustrative embodiments 14-15, wherein training the machine learning based task network for performing the medical analysis task comprises: training the machine learning based task network using a cost function that incorporates the self-supervised labels and the generated weakly-supervised labels.

Illustrative embodiment 17. The non-transitory computer readable medium of any one of illustrative embodiments 14-16, wherein the machine learning based task network comprises an encoder and a plurality of decoders and training the machine learning based task network for performing the medical analysis task comprises: training the machine learning based task network to perform a plurality of tasks performed respectively using one of the plurality of decoders.

Illustrative embodiment 18. The non-transitory computer readable medium of any one of illustrative embodiments 14-17, wherein the machine learning based task network comprises an encoder and a plurality of decoders and training the machine learning based task network for performing the medical analysis task comprises: training an initial decoder of the plurality of decoders to generate a reconstructed image based on features generated by the encoder; and training one or more additional decoders of the plurality of decoders to respectively perform one or more tasks based on the reconstructed image.

Illustrative embodiment 19. The non-transitory computer readable medium of any one of illustrative embodiments 14-18, wherein the machine learning based task network comprises an encoder and a plurality of decoders and training the machine learning based task network for performing the medical analysis task comprises: finetuning the machine learning based task network using one or more of the plurality of decoders for domain adaptation.

Illustrative embodiment 20. A computer-implemented method comprising: receiving unannotated training medical data; generating weakly-supervised labels for the unannotated training medical data using one or more trained machine learning based supervised learning networks; training a machine learning based task network for performing a medical analysis task based on 1) the unannotated training medical data, 2) self-supervised labels for the unannotated training medical data learned via self-supervised learning, and 3) the generated weakly-supervised labels for the unannotated training medical data; and outputting the trained machine learning based task network.

The invention claimed is:

1. A computer-implemented method comprising:

receiving input medical data;

performing a medical analysis task using a trained machine learning based task network based on the input medical data; and outputting results of the medical analysis task, wherein the trained machine learning based task network is trained by:

receiving unannotated training medical data;

generating weakly-supervised labels for the unannotated training medical data using one or more trained machine learning based supervised learning networks, wherein generating weakly-supervised labels for the unannotated training medical data using one or more trained machine learning based supervised learning networks comprises:

generating initial labels using the one or more trained machine learning based supervised learning networks, and filtering the initial labels using one or more out-of-domain probability distribution models to result in labels generated from input data that is in-domain of the one or more trained machine learning based supervised learning networks as the weakly-supervised labels;

training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data, wherein training the machine learning based task network for performing the medical analysis task comprises:

extracting latent features from the unannotated training medical data using an encoder of the machine learning based task network, assigning the generated weakly-supervised labels to the extracted latent features, and training the machine learning based task network based on the generated weakly-supervised labels assigned to the extracted latent features; and outputting the trained machine learning based task network.

2. The computer-implemented method of claim 1, wherein training the machine learning based task network for performing the medical analysis task comprises:

training the machine learning based task network using a cost function that incorporates the self-supervised labels and the generated weakly-supervised labels.

3. The computer-implemented method of claim 1, wherein training the machine learning based task network for performing the medical analysis task comprises:

fitting a probability distribution model to a latent space of the machine learning based task network to capture an uncertainty; and training the machine learning based task network based on the uncertainty.

4. The computer-implemented method of claim 1, wherein the machine learning based task network further comprises a plurality of decoders and training the machine learning based task network for performing the medical analysis task comprises:

training the machine learning based task network to perform a plurality of tasks performed respectively using one of the plurality of decoders.

5. The computer-implemented method of claim 1, wherein the machine learning based task network further comprises a plurality of decoders and training the machine learning based task network for performing the medical analysis task comprises:

training an initial decoder of the plurality of decoders to generate a reconstructed image based on features generated by the encoder; and training one or more additional decoders of the plurality of decoders to respectively perform one or more tasks based on the reconstructed image.

6. The computer-implemented method of claim 1, wherein the machine learning based task network further comprises a plurality of decoders and training the machine learning based task network for performing the medical analysis task comprises:

finetuning the machine learning based task network using one or more of the plurality of decoders for domain adaptation.

7. An apparatus comprising:

means for receiving input medical data;

means for performing a medical analysis task using a trained machine learning based task network based on the input medical data; and means for outputting results of the medical analysis task, wherein the trained machine learning based task network is trained by:

receiving unannotated training medical data;

generating weakly-supervised labels for the unannotated training medical data using one or more trained machine learning based supervised learning networks, wherein generating weakly-supervised labels for the unannotated training medical data using one or more trained machine learning based supervised learning networks comprises:

generating initial labels using the one or more trained machine learning based supervised learning networks, and filtering the initial labels using one or more out-of-domain probability distribution models to result in labels generated from input data that is in-domain of the one or more trained machine learning based supervised learning networks as the weakly-supervised labels;

training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data, wherein training the machine learning based task network for performing the medical analysis task comprises:

extracting latent features from the unannotated training medical data using an encoder of the machine learning based task network, assigning the generated weakly-supervised labels to the extracted latent features, and training the machine learning based task network based on the generated weakly-supervised labels assigned to the extracted latent features; and outputting the trained machine learning based task network.

8. The apparatus of claim 7, wherein training the machine learning based task network for performing the medical analysis task comprises:

training the machine learning based task network using a cost function that incorporates the self-supervised labels and the generated weakly-supervised labels.

9. The apparatus of claim 7, wherein training the machine learning based task network for performing the medical analysis task comprises:

fitting a probability distribution model to a latent space of the machine learning based task network to capture an uncertainty; and training the machine learning based task network based on the uncertainty.

10. A non-transitory computer readable medium storing computer program instructions, the computer program instructions when executed by a processor cause the processor to perform operations comprising:

receiving input medical data;

performing a medical analysis task using a trained machine learning based task network based on the input medical data; and outputting results of the medical analysis task, wherein the trained machine learning based task network is trained by:

receiving unannotated training medical data;

generating weakly-supervised labels for the unannotated training medical data using one or more trained machine learning based supervised learning networks, wherein generating weakly-supervised labels for the unannotated training medical data using one or more trained machine learning based supervised learning networks comprises:

generating initial labels using the one or more trained machine learning based supervised learning networks, and filtering the initial labels using one or more out-of-domain probability distribution models to result in labels generated from input data that is in-domain of the one or more trained machine learning based supervised learning networks as the weakly-supervised labels;

training the machine learning based task network for performing the medical analysis task based on 1) the unannotated training medical data, 2) self-supervised labels for the unannotated training medical data learned via self-supervised learning, and 3) the generated weakly-supervised labels for the unannotated training medical data, wherein training the machine learning based task network for performing the medical analysis task comprises:

extracting latent features from the unannotated training medical data using an encoder of the machine learning based task network, assigning the generated weakly-supervised labels to the extracted latent features, and training the machine learning based task network based on the generated weakly-supervised labels assigned to the extracted latent features; and outputting the trained machine learning based task network.

11. The non-transitory computer readable medium of claim 10, wherein training the machine learning based task network for performing the medical analysis task comprises:

training the machine learning based task network using a cost function that incorporates the self-supervised labels and the generated weakly-supervised labels.

12. The non-transitory computer readable medium of claim 10, wherein the machine learning based task network further comprises a plurality of decoders and training the machine learning based task network for performing the medical analysis task comprises:

training the machine learning based task network to perform a plurality of tasks performed respectively using one of the plurality of decoders.

13. The non-transitory computer readable medium of claim 10, wherein the machine learning based task network further comprises a plurality of decoders and training the machine learning based task network for performing the medical analysis task comprises:

training an initial decoder of the plurality of decoders to generate a reconstructed image based on features generated by the encoder; and training one or more additional decoders of the plurality of decoders to respectively perform one or more tasks based on the reconstructed image.

14. The non-transitory computer readable medium of claim 10, wherein the machine learning based task network further comprises a plurality of decoders and training the machine learning based task network for performing the medical analysis task comprises:

finetuning the machine learning based task network using one or more of the plurality of decoders for domain adaptation.

15. A computer-implemented method comprising:

receiving unannotated training medical data;

generating weakly-supervised labels for the unannotated training medical data using one or more trained machine learning based supervised learning networks, wherein generating weakly-supervised labels for the unannotated training medical data using one or more trained machine learning based supervised learning networks comprises:

generating initial labels using the one or more trained machine learning based supervised learning networks, and filtering the initial labels using one or more out-of-domain probability distribution models to result in labels generated from input data that is in-domain of the one or more trained machine learning based supervised learning networks as the weakly-supervised labels;

training a machine learning based task network for performing a medical analysis task based on 1) the unannotated training medical data, 2) self-supervised labels for the unannotated training medical data learned via self-supervised learning, and 3) the generated weakly-supervised labels for the unannotated training medical data, wherein training the machine learning based task network for performing the medical analysis task comprises:

extracting latent features from the unannotated training medical data using an encoder of the machine learning based task network, assigning the generated weakly-supervised labels to the extracted latent features, and training the machine learning based task network based on the generated weakly-supervised labels assigned to the extracted latent features; and outputting the trained machine learning based task network.

16. The computer-implemented method of claim 15, wherein training a machine learning based task network for performing a medical analysis task comprises:

training the machine learning based task network using a cost function that incorporates the self-supervised labels and the generated weakly-supervised labels.

17. The computer-implemented method of claim 15, wherein training a machine learning based task network for performing a medical analysis task comprises:

fitting a probability distribution model to a latent space of the machine learning based task network to capture an uncertainty; and training the machine learning based task network based on the uncertainty.

18. The computer-implemented method of claim 15, wherein the machine learning based task network further comprises a plurality of decoders and training a machine learning based task network for performing a medical analysis task comprises:

training the machine learning based task network to perform a plurality of tasks performed respectively using one of the plurality of decoders.

19. The computer-implemented method of claim 15, wherein the machine learning based task network further comprises a plurality of decoders and training a machine learning based task network for performing a medical analysis task comprises:

training an initial decoder of the plurality of decoders to generate a reconstructed image based on features generated by the encoder; and training one or more additional decoders of the plurality of decoders to respectively perform one or more tasks based on the reconstructed image.

20. The computer-implemented method of claim 15, wherein the machine learning based task network further comprises a plurality of decoders and training a machine learning based task network for performing a medical analysis task comprises:

finetuning the machine learning based task network using one or more of the plurality of decoders for domain adaptation.

* * * * *